(12) United States Patent
Sonnenberg et al.

(10) Patent No.: US 6,832,125 B2
(45) Date of Patent: Dec. 14, 2004

(54) PHOTOGRAPHS OF FABRICS AND METHODS FOR MAKING THEM

(75) Inventors: David Sonnenberg, Tenafly, NJ (US); Henricus Aldegonda Hendrikx, Beek en Donk (NL)

(73) Assignee: Hunes BV, El Rotterdam (NL)

( * ) Notice: Subject to any disclaimer, the term of this patent is extended or adjusted under 35 U.S.C. 154(b) by 227 days.

(21) Appl. No.: 09/996,117

(22) Filed: Nov. 27, 2001

(65) Prior Publication Data

US 2002/0064301 A1 May 30, 2002

Related U.S. Application Data

(60) Provisional application No. 60/253,175, filed on Nov. 27, 2000.

(51) Int. Cl.[7] ............................. G06F 19/00; G06K 9/00
(52) U.S. Cl. ....................................... 700/130; 382/111
(58) Field of Search ................................ 700/130, 143; 382/111; 356/238.1, 238.3, 429, 430

(56) References Cited

U.S. PATENT DOCUMENTS

| 4,550,038 A | * 10/1985 | Becker et al. ................. 428/12 |
| 4,998,489 A | * 3/1991 | Hisatake et al. ............ 112/103 |
| 5,193,185 A | 3/1993 | Lanter ........................ 395/600 |
| 5,497,335 A | 3/1996 | Hoeller ........................ 364/470 |
| 5,740,425 A | 4/1998 | Povilus ....................... 395/611 |
| 5,870,771 A | 2/1999 | Oberg ......................... 707/502 |
| 5,966,454 A | 10/1999 | Thomas et al. ............. 382/111 |
| 6,005,969 A | 12/1999 | Thomas et al. ............. 382/162 |
| 6,243,615 B1 | 6/2001 | Neway et al. .............. 700/108 |
| 6,415,045 B1 | * 7/2002 | Quigley et al. ............. 382/111 |

FOREIGN PATENT DOCUMENTS

EP 0 486 126 1/1992

* cited by examiner

*Primary Examiner*—Peter Nerbun
(74) *Attorney, Agent, or Firm*—Dorsey & Whitney LLP

(57) ABSTRACT

A method for reproducibly making photographs of different fabrics is provided. The method produces photographs which depict one or more characteristics of each fabric. Such characteristics include the texture, pattern, thickness, drape and translucency, each of which characteristics can be reliably understood and compared. The method comprises the steps of folding each fabric in the same way, placing the folded fabric on a background surface in order to provide the fabric with a standardized draped shape and then photographing each draped and folded fabric in the same way. Further, by utilizing digital photography the photographs for each fabric can be suitably viewed via an internet web site. Additionally, the photograph of each fabric can also be computer generated in a photo-realistic image depicting a likely or intended use of the fabric, for example, as drapery or a covering for furniture.

63 Claims, 6 Drawing Sheets

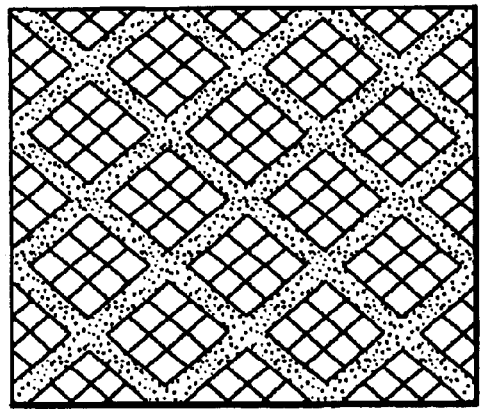
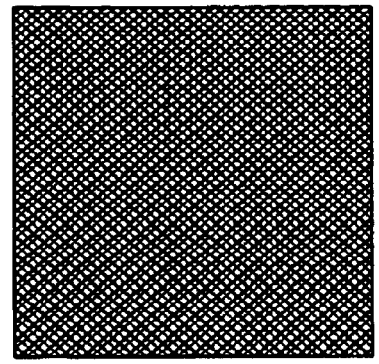
FIG.4A  FIG.4B
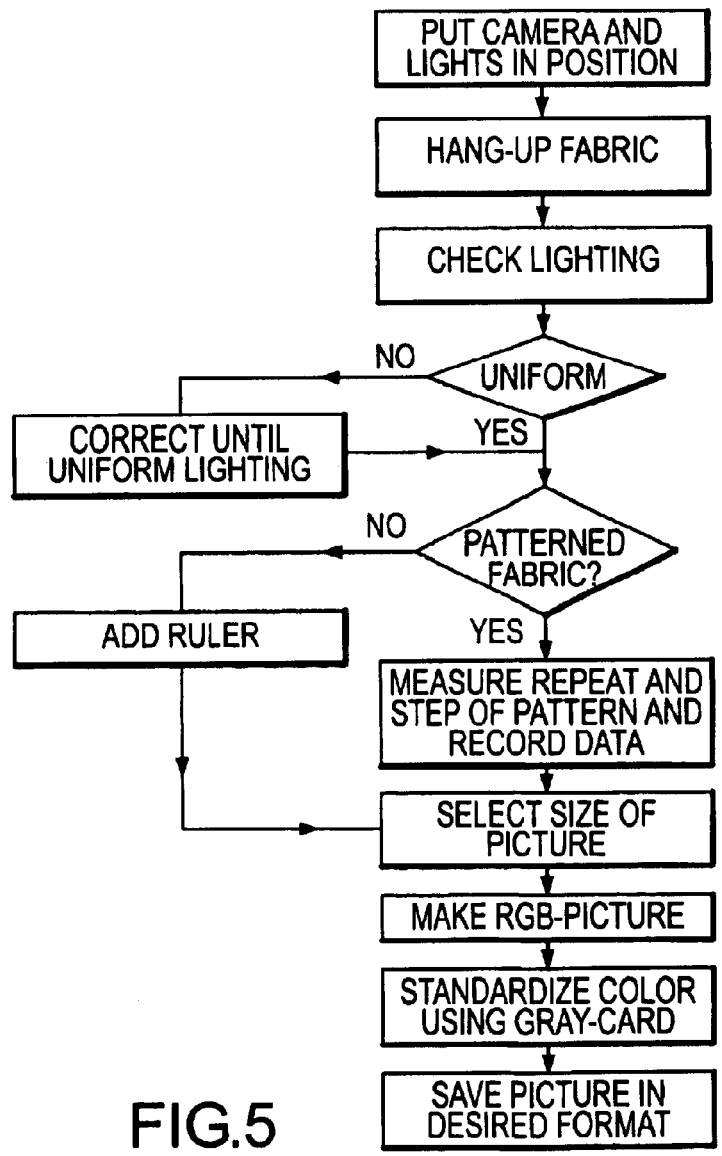
FIG.5

PHOTOGRAPHS OF FABRICS AND METHODS FOR MAKING THEM

CROSS REFERENCE TO RELATED APPLICATIONS

The present application claims priority to U.S. Provisional Patent Application Ser. No. 60/253,175, entitled "Photographs and Methods for Making Them", filed on Nov. 27, 2000 in the name of the inventors David Sonnenberg and Henricus Aldegonda Hendrikx, the contents of which are hereby incorporated by reference in their entirety.

FIELD OF THE INVENTION

This invention relates to photographs of fabrics which more accurately convey, to their viewers, particularly to fabric experts, information about each fabric's texture, pattern and thickness, as well as its drape and translucency. The invention particularly relates to photographs which can be viewed by potential fabric purchasers via an internet web site. The invention also relates to a standardized method of reproducibly making such photographs of different fabrics, so that the texture, pattern and thickness, as well as the drape and translucency, of each fabric can be reliably understood and compared.

BACKGROUND OF THE INVENTION

Buyers of fabrics generally like to select fabrics by choosing from among a large number of fabric swatches, i.e., samples. A potential buyer will generally look at each swatch of a fabric and examine its texture, pattern and thickness. The potential buyer will also feel the texture of the fabric swatch, see how the fabric drapes, and notice its translucency.

When a potential buyer is to select a fabric from a catalogue of fabrics or from electronic images of fabrics, e.g. on television or via the internet, the potential buyer can no longer touch the fabric, drape it or hold it to the light to determine its translucency.

Systems for photographing and digitizing photographs and then storing and displaying them, using computers, are known, e.g., from EP 0 468126 (for ceramics) and U.S. Pat. No. 5,966,454 and U.S. Pat. No. 6,005,969 (for fabrics). Using generally conventional computer software and hardware with high resolution graphics processing capabilities, a user may view and even modify colors of the photographed designs on the user's computer screen.

However, photographing, digitizing and storing a photographic image of a fabric, so that a buyer is then likely to decide to buy the fabric or at least to ask for a swatch of the fabric before deciding to buy it, is more than just a technical problem. The fabric's photographic image should convey a maximum amount of information about the texture, color, thickness, pattern and drapability of the fabric.

SUMMARY OF THE INVENTION

The problem of conveying the maximum amount of information with a minimum number of pictures has been solved by the standardized method of this invention for reproducibly making photographs of different fabrics, so that one or more of each fabric's characteristics of texture, pattern, thickness, drape and translucency can be reliably understood and compared. The method comprises the steps of: folding each fabric in the same way; placing the folded fabric on a background surface to provide it with a standardized draped shape; and then photographing each draped and folded fabric in a first same way.

Advantageously, each fabric has one to three folds, preferably two folds. Also advantageously, each fabric is photographed, so that the resulting photograph has a first total surface area, a second surface area of the photograph shows the fabric and a third surface area of the photograph shows the background surface; the second surface area being greater than the third surface area. Further advantageously, each fabric has two folds; and the predetermined standardized drape of the fabric comprises: a bottom ply that is on the background surface and has a first side edge; an intermediate ply having a second side edge; a first fold line between the bottom and intermediate plies; and a top ply having a third side edge; and a second fold line between the intermediate and top plies; wherein the first, second and third side edges are on the same side of the fabric; the first and third side edges are spaced apart and extend generally parallel in a first direction; the second side edge is located between the first and third side edges; and the first and second fold lines are spaced apart and extend generally parallel in a second direction, that is preferably substantially perpendicular to the first direction. It is particularly advantageous that the first, second and third side edges are serrated.

Advantageously, each fabric is also photographed in a second same way as straight with a full-repeat of a pattern, advantageously with a serrated edge and atop a gray background.

Advantageously, each fabric is further shown in a computer-generated photo-realistic image in a third same way, in use, particularly as a window covering and/or a furniture covering.

Also in accordance with this invention, a photograph has been made by the above-described method. The photograph can be shown as an image on an internet web site.

Further in accordance with this invention, a method of assessing the texture, pattern, thickness, drape and/or translucency of a fabric is provided, comprising the step of viewing the just-described photograph.

BRIEF DESCRIPTION OF THE FIGURES

Further aspects of the invention will be apparent from the detailed description below of a particular embodiment and the drawings thereof, in which:

FIGS. 4A and 4B are each a picture, for identification purposes, of a sample of a flat or straight fabric (which is the same fabric shown in FIG. 2B); the fabric in FIG. 4B comprises a full repeat on gray with serrated edges;

FIG. 5 is a flow chart, showing the steps of a method of photographing a sample of a flat fabric (e.g., as in FIGS. 4A and 4B) according to the invention;

DETAILED DESCRIPTION OF THE INVENTION

Figure 1:
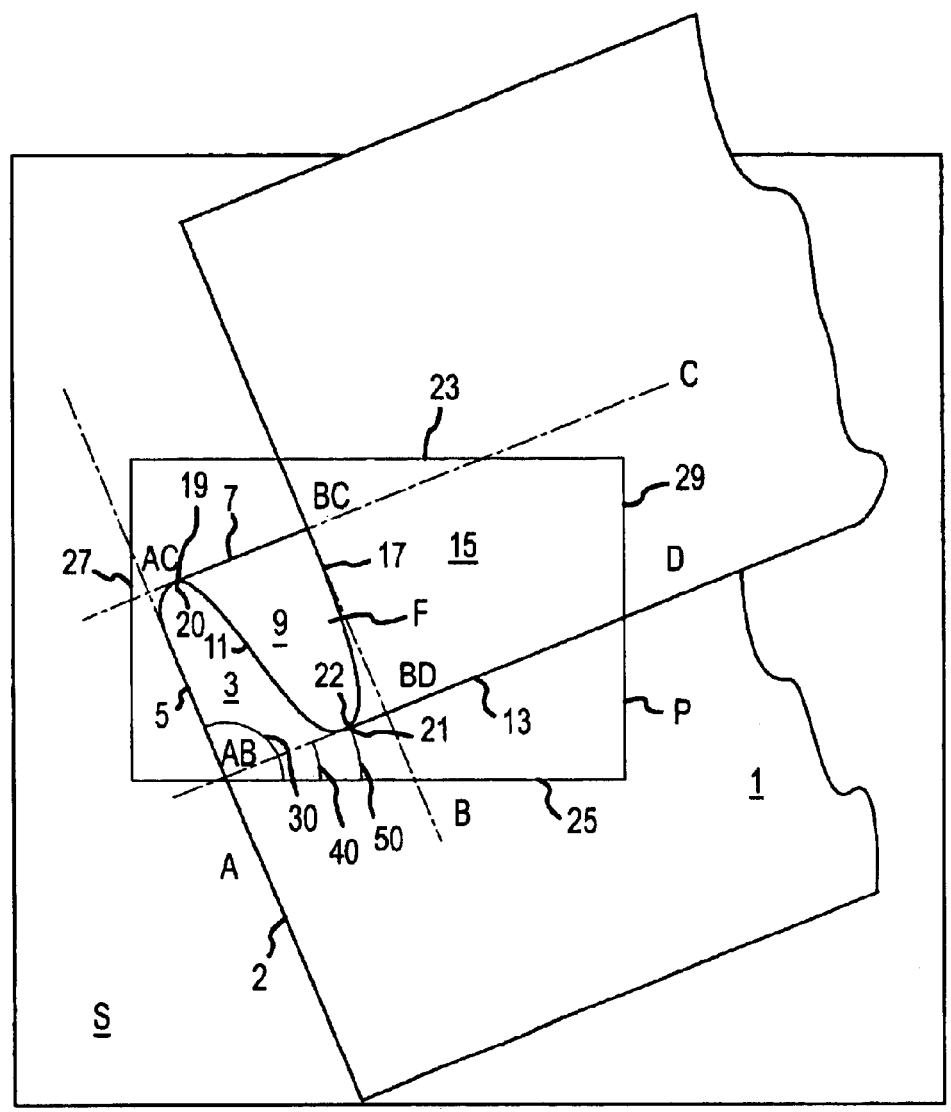
FIG. 1 is a schematic representation of a standard method of draping a sample of a fabric, to be photographed according to the invention.
Figure 2A:
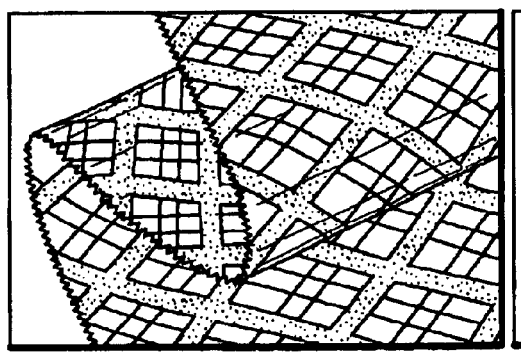
FIGS. 2A and 2B are each a picture of a different, draped fabric according to the invention, showing its different texture, pattern and thickness, as well as its drape and translucency.
Figure 2B:

FIG. 1 schematically shows a standard method for draping a sample of a fabric 1, that is to be photographed according to the invention as shown in FIGS. 2A and 2B. The resulting photograph or image of the draped fabric 1 can be shown on an internet web site, so that experienced fabric buyers will be able to see the fabric's texture, pattern and thickness, as well as its drape and translucency and be able to compare reliably these qualities of the fabric 1 with the same qualities of other different fabrics, draped and photographed in the same way.

The standardized draping method of FIG. 1 involves folding the fabric sample 1 transverse to its side edge 2 to form:

a bottom ply or portion 3 having a first side edge 5;

a first fold line 7;

an intermediate ply or portion 9 having a second side edge 11;

a second fold line 13; and a top ply or portion 15 having a third side edge 17.

This folding procedure is carried out so that the resulting fabric sample 1 has a generally sinusoidal (wave-like) shape comprising two gentle curves 19, 21—with no hard creases. The first or bottom curve 19 is formed in the fabric where the first fold line 7 takes shape, between the first and second side edges 5, 11, and the second or top curve 21 is formed in the fabric where the second fold line 13 takes shape, between the second and third side edges 11, 17. The first curve 19 has a first radius 20 where the first fold line 7 is formed. The second curve 21 has a second radius 22 where the second fold line 13 is formed. Preferably the first radius 20 is smaller than the second radius 22.

This double-folded fabric sample 1 is then positioned on a flat horizontal background surface S having the same color and surface texture for each fabric photographed. Only part of the underlying surface S falls within the actual photograph of the fabric sample 1 as is shown by a virtual picture frame P in FIG. 1. As shown in FIG. 1, the virtual picture frame P has a top side 23, a bottom side 25 (closest to a camera [not shown] which will take a photo of the folded fabric 1), a left side 27 and a right side 29. The fabric sample 1 is positioned on the surface S with its first and third side edges 5,17 spaced apart and extending generally parallel to each other. The first and third side edges 5,17 extend in a first direction which is at an obtuse angle 30, relative to the bottom side 25 of the virtual picture frame S. The second side edge 11 of the fabric is always located between its first and third side edges 5,17 in the virtual picture frame P and is, therefore, always shown to a viewer in the frame P. The shown surface of the intermediate ply 9 of the fabric 1, extending in the plane between its second and third side edges 11, 17, is actually the rear surface of the fabric sample 1. The first and second fold lines 7,13 are also spaced apart and extend generally parallel to each other. The first and second fold lines 7,13 extend in a second direction which is substantially perpendicular to the first direction of the first and third side edges 5,17. The second direction is at an acute angle 40 relative to the bottom side 25 of the virtual picture frame S.

Preferably, the obtuse angle 30 of the first direction of the resulting double-folded draped fabric sample 1, relative to the bottom side 25 of the virtual picture frame P, is between about 105° and 120°, especially about 110°. The second direction of the draped fabric sample 1, being substantially perpendicular to the first direction, is therefore preferably at an acute angle between about 15° and 30°, especially about 20°, relative to the bottom side 25 of the virtual picture frame P.

In FIG. 1, auxiliary lines A and B are drawn along the first and third side edges 5,17, respectively, in the first direction of the double-folded draped fabric sample 1 and continue in the same parallel direction. Auxiliary lines C and D are drawn along the first and second fold lines 7,13, respectively, of the double-folded fabric sample 1 and continue in the same parallel direction. These auxiliary lines A,B,C,D are drawn to clarify the standardized shape of the fabric sample 1 in the virtual picture frame P containing the fabric's standardized two folds. Auxiliary lines A, B, C, D intersect at points AB, AC, BC and BD, thus creating a virtual fold frame F, within which the two-ply fold is located. The virtual fold frame F is preferably generally rectangular. The virtual fold frame F stands in the virtual picture frame P under an acute angle 50, that is off set from the bottom side 25 of the virtual picture frame. The acute angle 50 is equal to the acute angle 30 of the first direction of the first and third side edges 5,17 and is, therefore, preferably between about 15° and 30°, especially about 20°.

The surface area of the virtual fold frame F is smaller than the surface area of the virtual picture frame P. Preferably, the ratio of the surface area of the virtual fold frame F to the surface area of the virtual picture frame P is between about 15:100 and 30:100, especially about 20:100.

The shown side edges 5, 11,17 of the double-folded draped fabric sample 1 in FIG. 1 are inter-connected and form part of the total side edge of the fabric sample. The shown side edges 5, 11,17 are preferably serrated.

In order to create a photograph, like FIGS. 2A and 2B with the standardized drape of the fabric sample 1—so that a fabric expert can clearly see and appreciate its texture, pattern, thickness, drape and translucency and, perhaps even more importantly, see and appreciate its differences in texture, pattern, thickness, drape and translucency from other fabrics draped and photographed in exactly the same way—the fabric sample 1 should be folded and draped exactly as described above.

This can be accomplished, in a relatively easy way, by making a mask exactly like the double-folded draped fabric sample 1 of FIG. 1 and projecting this mask onto a computer monitor. Then with the use of a suitable camera, a life-sized image of the double-folded draped fabric sample 1 can be projected on the monitor. By superimposing the mask of the displayed fabric 1 and by filming another fabric as it is being draped, feed back is provided to the person draping the other fabric. When the fold and drape of the other fabric match the mask lines of the fabric 1 on the monitor, the picture of the other fabric can be taken.

Another method of draping a fabric, like the draped fabric 1 of FIG. 1, is by putting guiding lines on a surface, on which the other fabric rests and then draping the other fabric accordingly. A special tool having the general shape of a "U" can be used to assist in draping. The U-shaped tool should have a first leg and a second leg, with the first leg having a circular cross-section similar in size to the interior of the first fold line curve 19 and the second leg having a circular cross-section similar in size to the interior of the second fold line curve 21. The legs of the U-shaped tool should be long enough to drape the fabric about it but short enough to remain hidden by the fabric. Instead of a special U-shaped tool, simple circular rods of cardboard or other material could be used to shape the fold line curves 19, 21.

Yet another way of draping a fabric, like the draped fabric 1 of FIG. 1, is by projecting the desired drape-shape on a surface, on which the fabric rests, then putting the fabric on the surface and draping it along the projected lines. Use of the U-shaped tool or the circular rods, mentioned above, would, of course, be possible as would some combination of the foregoing methods.

FIGS. 2A and 2B show two different draped fabric samples 1 of the invention, with their different textures, patterns, thicknesses, drape and translucency. To make each picture, its fabric sample 1 is positioned on the surface S and is draped in the previously described two-ply fold. A standard gray card can then be positioned on the surface S, next to the fabric 1. This card shows the standard colors: gray, white and black. A photograph of the draped fabric is then taken, preferably using a conventional digital camera with software for color management (e.g. LeafCapture 5.2 of Scitex). The photograph could also be taken by a normal camera and subsequently digitized by a scanner. The resulting digital image is fed to a computer, preferably with a big screen (e.g., a cyberscreen 21 inch). After making a black and white preview to check that the image is sharp, a shot is taken in conventional HDR-format. This is actually a three-fold shot for the separate color channels, red, green and blue. The colors are calibrated by calibrating the gray column of the gray card.

The camera lights, used for lighting the fabric sample 1 and the position and the angle of the camera relative to the surface S on which the fabric rests, should also be kept constant. The camera angle is preferably 45° downward and straight at the fabric sample, the distance to the focus-point is preferably 77 cm, the diaphragm is set at "8", and the height above the surface S is 45 cm. Generally, two lights are used, a main light and a auxiliary light, both with a maximum capacity of 3200 joules. Lighting of each fabric sample 1 should be as constant as possible and be checked with a standard light measuring device on several positions on each fabric (since some fabrics, like velours, absorb a lot of light). Lighting problems can also be corrected in a conventional manner, such as by positioning white and black boards on standards close to the fabric or positioning a third light above the fabric sample if the fabric absorbs a lot of light and measuring the lighting of the fabric again. Each light is at a different position relative to the surface S where the fabric rests. The main light is positioned at a distance of 140 cm from the fabric, at a leftward angle of 30° relative to the fabric, at a downward angle of 40°, and at a height of 97 cm above the surface S. The auxiliary light is positioned at a distance of 80 cm from the fabric, at a rightward angle of 30° relative to the fabric, at a height of 106 cm above the surface S and angled downwardly at an angle of 40°.

Figure 9A:
FIG. 9A is a computer-generated view for a window covering fabric, with several separate views showing the draped fabric (of FIG. 2A), the same fabric as a flat fabric (as in FIGS. 4A and 4B) and the same fabric in a computer-generated rendering of a window covering (as in FIG. 6)
Figure 9B:
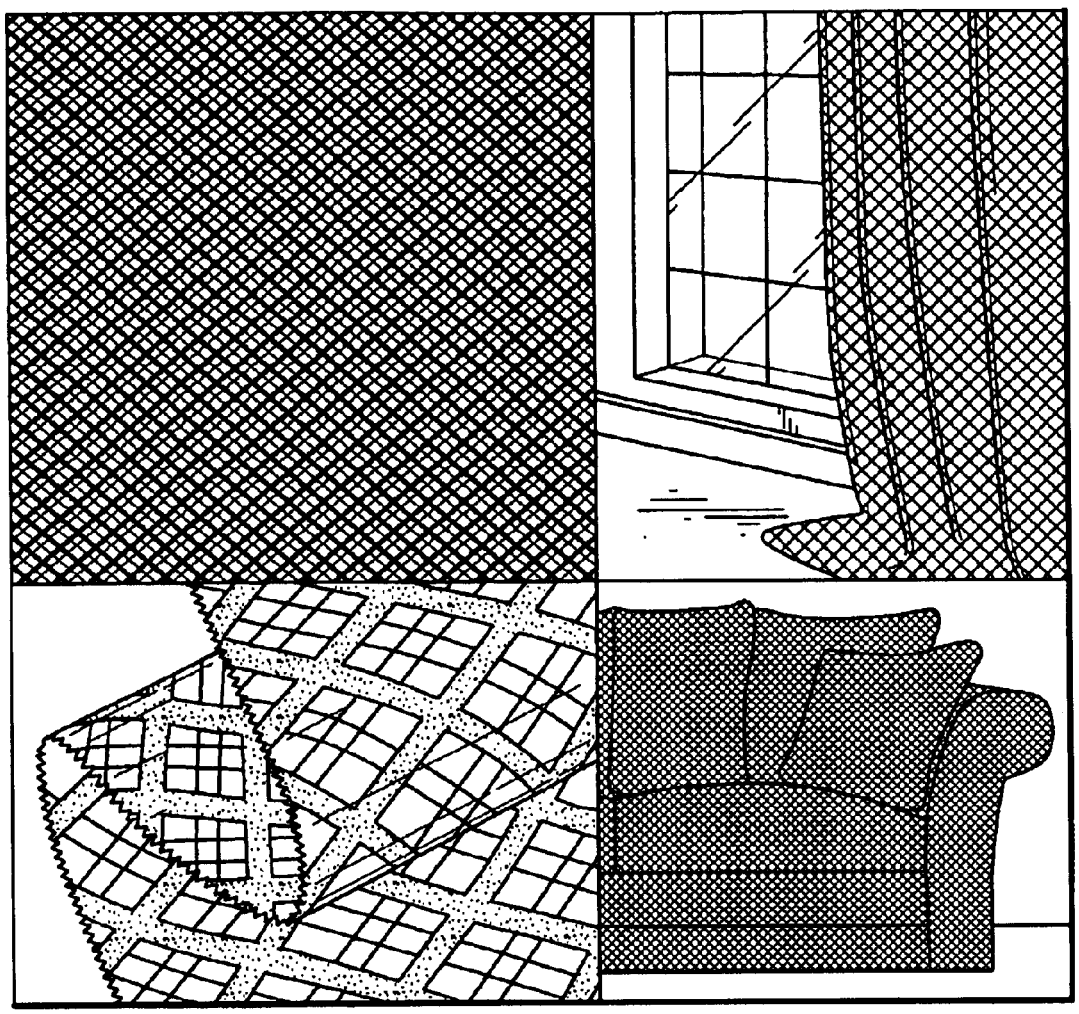
FIG. 9B is a computer-generated view for a multi-purpose (e.g., for furniture and window coverings) fabric, with several separate views showing the draped fabric (of FIG. 2B), the same fabric as a flat fabric (as in FIG. 4A), the same fabric in a computer-generated rendering of a window covering (as in FIG. 6) and the same fabric in a computer-generated rendering of a couch.
Figure 9C:
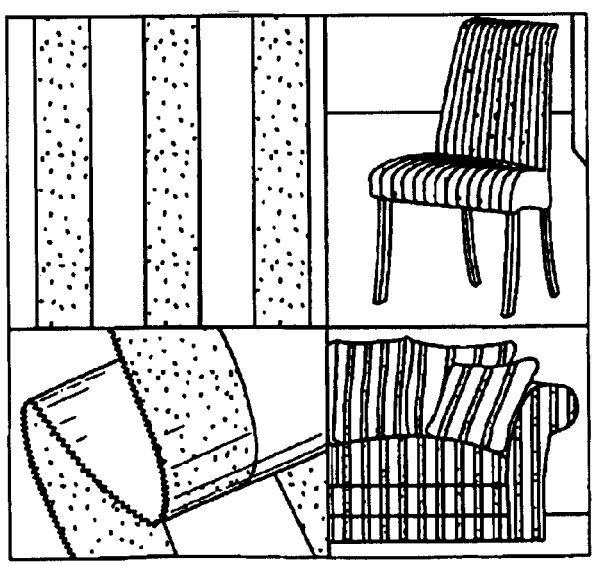
FIG. 9C is a computer-generated view for a furniture fabric, with several separate views showing a draped fabric (as in FIGS. 2A and 2B), the same fabric as a flat fabric (as in FIGS. 4A and 4B), the same fabric in a computer-generated rendering of a chair (of FIG. 8) and the same fabric in a computer-generated rendering of a couch.

Once the photograph is taken, it can be transferred to paper in a catalogue of fabrics or, more conveniently, it can be stored in a computer and digitized for use in a computer database or in an on-line internet web site. The photo can then be used for viewing the general texture and drapability of the fabric and also information as to its color, translucency and thickness. Relevant identifying data, such as the fabric name and its manufacturer's and/or vendor's numbers, can be printed on the photo or can be virtually tagged to the photo when stored in a computer. When used by a computer, the photo also can be digitally altered to better fit different display modes. In this regard, its size can be changed, for example to a thumbnail photo size for display of search results to a bigger size when a full-view is requested. Another size can also be used when the photo is to be displayed as one view in a multi-view format as in FIGS. 9A, 9B and 9C.

Figure 3:
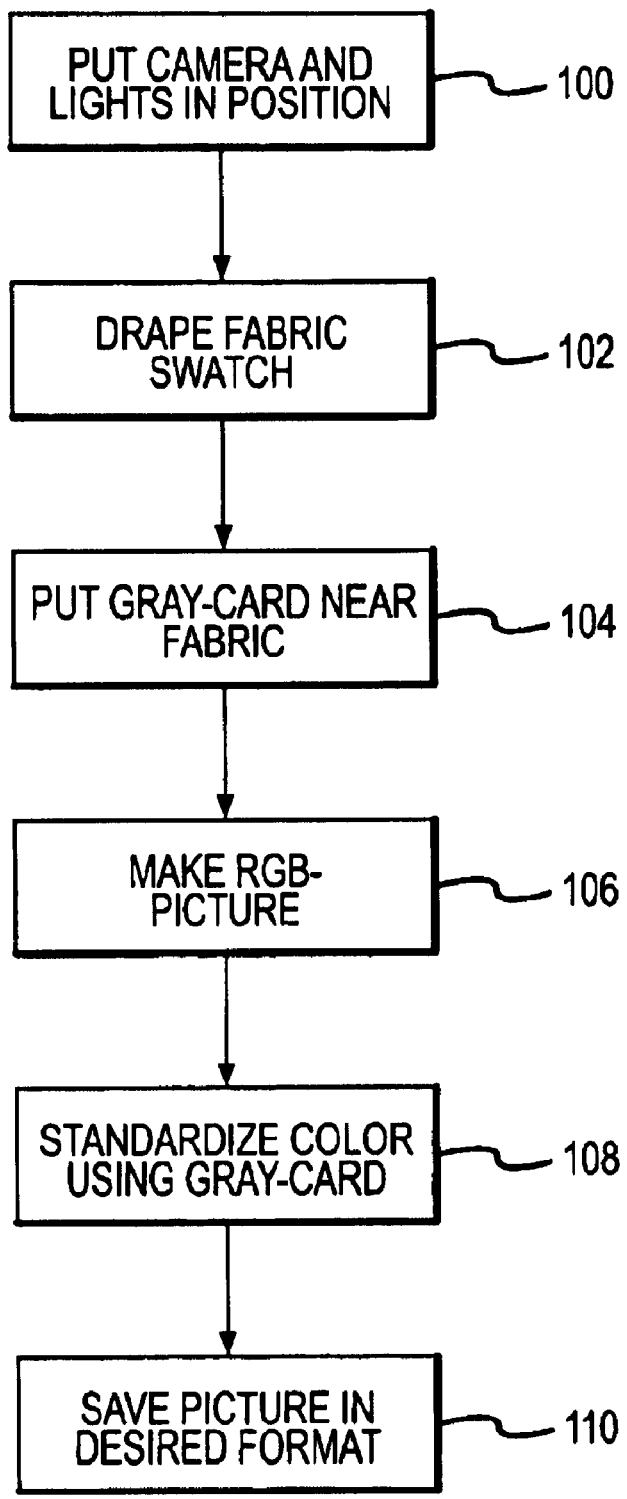
FIG. 3 is a flow chart, showing the steps of a method of photographing a sample of a draped fabric (e.g., as in FIGS. 2A and 2B) according to the invention.

FIG. 3 schematically shows a general flow chart of a process which can be used for making a photo of a draped fabric sample 1 as in FIGS. 2A and 2B. In a first step 100, camera and lights are put in their proper standard position as described above, relative to the horizontal surface S, on which the fabric 1 is to be draped. In a second step 102, drape the fabric sample 1 is draped in the standard two-ply drape as described above. In a third step 104, the gray-card described above is placed in the same place on the surface S next to the fabric 1. In a fourth step 106, the photo is taken of the folded fabric 1. In a fifth step 108, the color of the photo is standardized in a conventional manner, using the gray card. In a sixth step 110, the photo is stored in the desired format and preferably any tags with desired information are affixed to the photo.

FIGS. 4A and 4B are photos showing a straight or flat (i.e., not folded) sample of a fabric with a full-repeat of its pattern. The fabric in FIG. 4B is shown on a gray background and has a serrated edge, both of which features preferably are computer generated. The photos provide readily understandable information on the size of the pattern relative to the standard size of the serrations.

These photos are made by hanging the fabric downwardly form one edge. If the fabric has a repeating pattern, the size of one pattern repeat is measured, and the repeat direction (horizontal, vertical, angle) and its size are determined and recorded. A photo is taken of a portion of the fabric, showing the pattern and optionally some repeats. For example, if a pattern has a repeat of up to 9×9 cm, a 25×25 cm portion of the fabric is photographed. (This is called a small-repeat.) If a pattern has a repeat of between 9×9 cm and 55×55 cm, a 70×70 cm portion of the fabric is photographed. (This is called a medium-repeat.) If a pattern has a repeat of bigger than 55×55 cm, a 80×80 cm portion of the fabric is photographed. (This is called a big repeat.)

These photograph sizes can, however, be varied for convenience in photographing many fabrics.

When making these photos, a standard gray-card is positioned next to the fabric in the same spot for every photo. If a one-color fabric is used, then a ruler or similar measuring instrument is also positioned next to the fabric to give an idea of its size.

The steps and equipment used in making these photos are generally the same as were described above for FIGS. 2A and 2B. However, the camera is level and not angled.

FIG. 5 schematically shows a general flow chart of the process, just described, which can be used for making a photo of a straight sample of a fabric with a full-repeat of its pattern as in FIGS. 4A and 4B. FIG. 4B is preferably made in a conventional manner as a computer processed rendering of the fabric of FIG. 4A with different sizes of serrations being provided for different sizes of the pattern repeat in order to give the viewer an idea of the size of the pattern.

Figure 6:
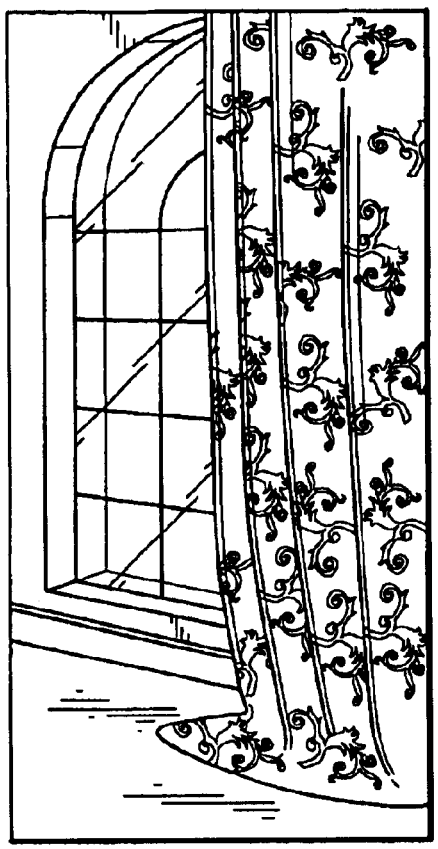
FIG. 6 is a computer-generated rendering of a fabric as a window covering.
Figure 7:
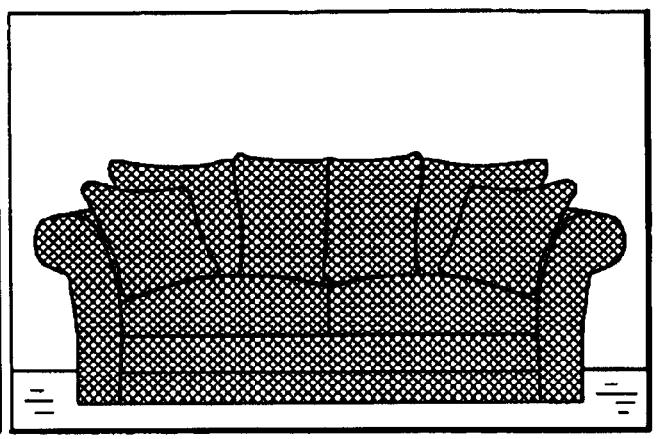
FIG. 7 is a computer-generated rendering of a fabric as a covering for a couch.
Figure 8:
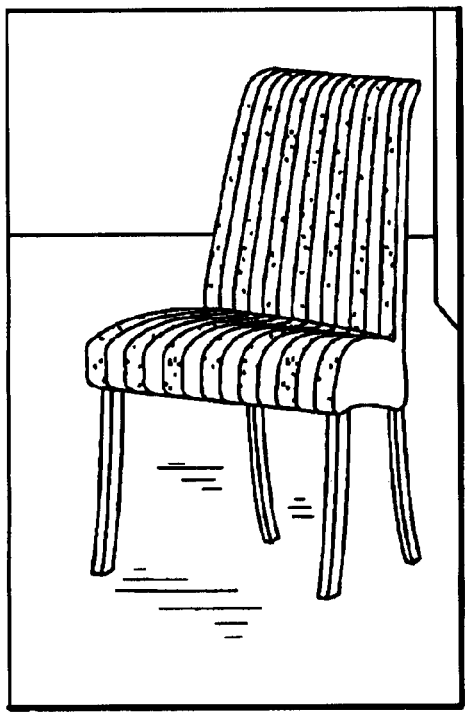
FIG. 8 is a computer-generated rendering of a fabric as a covering for a chair.

However, these photos of draped samples and straight samples of fabrics do not give a viewer an impression of the way the fabrics would look in actual use, for example, as window coverings and/or furniture coverings. For this reason, the viewer is also preferably provided with additional computer-generated photos as shown in FIGS. 6–8. These additional photos are photo-realistic views made by on-demand renderings of the photos of draped samples and/or straight samples of fabrics on 3D-digitized models of window coverings or furniture coverings.

The photos of fabrics used as window coverings (FIG. 6) and/or furniture coverings (FIGS. 7 and 8) can be made in generally conventional ways, using conventional software and computer hardware and stored fabric photos and 3-dimesnional (i.e., 3D) digitized models in the computer database. In this regard, a computer system can executes a search in a digital library containing identification photographs of fabric samples. After selecting several fabrics, the user can ask for photo-realistic views of a window covering, covered furniture, or view of both. The views can be rendered online by computer (e.g., via the internet), provided the identification photographs of the fabric samples are stored in a database, from which the computer can generate photo representations of the fabric in use as a window covering and/or a furniture covering.

FIGS. 6–8 each show computer generated photo-realistic representations of fabrics in use as a window covering or furniture covering in accordance with this invention. Each representation comprises a computer 3D model of the window covering or furniture, on which a fabric from a photo in a database has been applied by a process as described below. The representations can each be viewed as a computer-generated image on the screen of a conventional computer monitor.

The photo-realistic representations can be made by initially making a digital 3D model collection, using computer models showing the desired actual uses of fabrics as window coverings and furniture coverings. The digital 3D models can be processed from photographed model window coverings and covered furniture, using conventional graphics software. Each model can show the same view of a standard window with a standard window covering or a standard piece of covered furniture in a standard setting (e.g., a curtain for a window or a couch or a chair in room). Several different basic fabrics can be used for the models, but none should be painted or patterned. This is because the models are used only to establish basic views of window and furniture coverings, using certain different types of fabrics (e.g., heavy, light, bright, dark, easy plyable or not, translucent or not, etc.) for comparison with actual fabrics, to be used later on the models. For example, different 3D models of a single standard window covering can be made by using fabrics of different intensities of brightness. To add to the number of 3D models, each fabric of a certain intensity of brightness on a 3D model can be shown in different translucencies (i.e., each basic fabric can be shown with 20 different intensities of brightness on a 3D model, and for each intensity of brightness of the fabric on a model, the model can be shown in 10 different translucencies, so as to generate 200 different 3D window covering models). The same can be done for dark (non-painted) fabrics which are often heavier fabrics and have different translucencies.

Along similar lines, only excluding translucency, 3D furniture models can be created and stored in a database. Each 3D model can have three basic characteristics model. The first can be the model's use, preferably as a window or furniture covering, which can be represented as either W or R. The second can be whether the model is bright or dark which can be represented with B or D, together with a figure indicating the order of brightness or darkness (e.g., B1 or B9, D2 or D4). The third can be the model's translucency which can be represented with a T, together with a figure indicating the level of translucency (e.g. T1, T0, T10 etc). A dark model can, for example, be classified as WFD5T0, indicating that the model can be used as a window covering and as a furniture covering, is dark at a scale 5, and is not translucent.

Theoretically, each possible fabric can then be viewed on 400 different models. However, it is considered preferable to select the model best suited to display each fabric on. This can be done by also classifying each fabric swatch in the categories of use, bright/dark and translucency. The first characteristic can be the fabric's suitability of use for window and/or furniture coverings, which can be represented as W or R. The second characteristic can be whether the fabric is bright or dark which can be represented with B or D together with a figure indicating the order of brightness or darkness of the fabric (e.g., B1 or B9, D2 or D4). The third characteristic can be the fabric's translucency, which can be represented with a T, together with a figure indicating the level of translucency (e.g. T1, T0, T10 etc.) A dark fabric can, for example, be classified as WFD5T0, indicating that the fabric can be used as window covering and as furniture covering, is dark at a scale 5, and is not translucent. The appropriate 3D models can, therefore, be models classified as WFD5T0, WD5T0 and FD5T0.

Other classification indicia can be added to the system, such as indicia of the type of weave or basic material (cotton, nylon etc.) of the fabric. However this would not result in better representations, unless additional 3D models are created, showing these characteristics. In this regard, the possibilities of other indicia are virtual endless but are not preferred because they would result in the need for an enormous number of additional 3D models without greatly improving the end-result of the on-line generated photo-realistic representations of fabrics, in use.

Preferably, the fabric photographs stored in the database are photos or other images of draped fabric samples as described above with respect to FIGS. 1 and 2 and/or of straight fabric samples as described above with respect to FIG. 4, and each photo is tagged to indicate the eventual uses of its fabric. Thereby, conventional software can then be used to have a computer automatically generate an appropriate photo-realistic representation of each fabric in use, for example, as a window covering if the fabric is tagged for use as a window covering and the viewer requests a view of a window covering (e.g., by clicking an appropriate icon or selection screen on an online computer interfacing with the internet). Additional tagged information for each of the photos of draped or straight fabrics can indicate the fabric's relative brightness and/or translucency. Thereby, conventional software can be used to have a computer automatically generate a photo-realistic representation of each fabric in use as an appropriately bright and/or translucent window covering. If a viewer requests a furniture covering, the computer will generate a furniture view if the fabric has been tagged for such use.

Besides generating single view, photo-realistic representations of fabrics, a computer can also create multi-view representations of fabrics in accordance with this invention. See FIG. 9. Such multi-view representations preferably each comprise 2 or more, preferably 3 or 6, especially 4, photos or images of a single fabric. One photo thereof is preferably of a draped folded fabric sample 1 as in FIGS. 1 and 2, and another photo thereof is of a straight fabric sample as in FIG. 4. With these two basic views is provided one or more, additional computer-generated photo-realistic representations of the fabric in use. If the fabric can be used as a window covering and also as a furniture covering, the additional representations will include one or more computer-generated photos showing the fabric as a window-covering and one or more computer-generated photos showing the fabric as a furniture covering. See FIG. 9B. If the fabric can be used only as a window covering, the additional representations will only include one or more computer-generated photos showing the fabric in use as a window covering. See FIG. 9A. If the fabric can only be used as a furniture covering, the additional representations will only include one or more computer-generated photos showing the fabric in use as a furniture covering. See FIG. 9C.

In accordance with this invention, such additional representations of the fabric in use are preferably not stored, as such, in a database, such as the data base of an internet web site. Rather, these additional representations are created and displayed on an internet web site only when a potential customer of the fabric demands, on-line, views of the fabric.

This invention is intended to provide a plurality of standardized photographs or equivalent images of individual fabrics in the data base of a system, such as an internet web site for selling the fabrics, so that potential purchasers of the fabrics can accurately and reliably compare the fabrics from their photographs. In order to accomplish this, the only variable in each photo should be the fabric itself, not how it is photographed or represented. However, such standardized photographic representations of individual fabrics is often not sufficient for the purposes of fabric purchasers. For this reason, the standardized photographs of this invention are also adapted to allow a potential purchaser of the fabrics to discern accurately and reliably from the photos, certain characteristics of the fabrics, particularly their texture, pattern thickness, drape and translucency.

In this regard, the view of a draped double-folded fabric as in FIGS. 2 and 9 gives a lot more information than does a flat view as in FIG. 4, particularly as to the fabric's texture, drapability and translucency. Indeed, this draped view is like a 3-dimensional representation of the fabric because it conveys an idea of how the fabric feels when touched. Additional specific information about the fabric's pattern and repeat of a pattern is preferably provided by the additional view of a straight fabric sample as in FIG. 4. Furthermore, since images of a small sample make it difficult to visualize how a fabric would actually appear in use as a window covering or furniture covering, one or more additional computer-generated photo-realistic views are preferably provided, computer showing the fabric as a furniture covering and/or window covering as in FIGS. 6–9. Such views are particularly useful where the purchaser wishes to find a fabric of one design and color for different uses, such as both a window covering and a furniture coverings, to create a color-coordinated interior.

The photos or views, made by this invention, can be printed on paper and arranged in a conventional catalogue, advertising circular or the like. The photos can also be displayed on a conventional computer monitor and stored in a conventional digital library. In this regard, the method of this invention can be carried out with conventional computer hardware and software and, if desired, via the worldwide internet.

This invention is, of course, not limited to the above-described embodiments which can be modified without departing from the scope of the invention or sacrificing all of its advantages. In this regard, the terms in the foregoing description and the following claims, such as "top", "bottom", "vertical", "horizontal", "left" and "right", have been used only as relative terms to describe the relationships of the various elements of the photograph and the method of making the photograph of this invention. For example, each draped fabric sample 1, that is photographed, need only have at least one fold, but preferably has 1–3 folds, especially 2 folds. Also, the fabric, being photographed could be a woven, knit or non-woven fabric. Furthermore, the photo of each fabric could be made using a silver halide or other chemical based film but is preferably made electronically (i.e., is a digital image). Moreover, each fabric can be shown in computer-generated images for uses other than as window and/or furniture coverings, such as bed linen, table cloths, towels, etc.

What is claimed is:

1. A standardized method of reproducibly making photographs of different fabrics, so that one or more of each fabrics characteristics of texture, pattern, thickness, drape and translucency, can be reliably understood and compared, comprising the steps of: folding each fabric in the same way such that each fabric has two folds; placing the folded fabric on a background surface to provide it with a standardized draped shape wherein the predetermined standardized drape of the fabric comprises: a bottom ply that is of the background surface and has a first side edge; an intermediate ply having a second side edge; a first fold line between the bottom and intermediate plies; and a top ply having a third side edge; and a second fold line between the intermediate and top plies; wherein the first, second and third side edges are on the same side of the fabric; the first and third side edges are spaced apart and extend generally parallel in a first direction; the second side edge is located between the first and third side edges; and the first and second fold lines are spaced apart and extend generally parallel in a second direction; and then photographing each draped and folded fabric in a first same way, wherein each fabric is photographed, so that the resulting photograph has a first total surface area, a second surface area of the photograph shows the fabric and a third surface area of the photograph shows the background surface; the second surface area being greater than the third surface area.

2. A standardized method of reproducibly making photographs of different fabrics, so that one or more of each fabric's characteristics of texture, pattern, thickness, drape and translucency, can be reliably understood and compared, comprising the steps of: folding each fabric in the same way such that each fabric has one to three folds; placing the folded fabric on a background surface to provide it with a standardized shape, wherein the predetermined standardized drape of the fabric comprises: a bottom ply that is on the background surface and has a first side edge; an intermediate ply having a second side edge; a first fold line between the bottom and intermediate plies; and a top ply having a third side edge; and a second fold line between the intermediate and top plies; wherein the first, second and third side edges are on the same side of the fabric; the first and third side edges are spaced apart and extend generally parallel in a first direction; the second side edge is located between the first and third side edges; and the first and second fold lines are spaced apart and extend generally parallel in a second direction; and then photographing each draped and folded fabric in a first same way.

3. A standardized method of reproducibly making photographs of different fabrics, so that one or more of each fabric's characteristics of texture, pattern, thickness, drape and translucency, can be reliably understood and compared, comprising the steps of: folding each fabric in the same way such that each fabric has one to three folds; placing the folded fabric on a background surface to provide it with a standardized draped shape, wherein the predetermined standardized drape of the fabric comprises: a bottom ply that is on the background surface and has a first side edge; an intermediate ply having a second side edge; a first fold line between the bottom and intermediate plies; and a top ply having a third side edge; and a second fold line between the intermediate and top plies; wherein the first, second and third side edges are on the same side of the fabric; the first and third side edges are spaced apart and extend generally parallel in a first direction; the second side edge is located between the first and third side edges; and the first and second fold lines are spaced apart and extend generally parallel in a second direction; and then photographing each draped and folded fabric in a first same way, wherein each fabric is photographed, so that the resulting photograph has a first total surface area, a second surface area of the photograph shows the fabric and a third surface area of the photograph shows the background surface; the second surface area being greater than the third surface area.

4. A standardized method of reproducibly making photographs of different fabrics, so that one or more of each fabric's characteristics of texture, pattern, thickness, drape and translucency, can be reliably understood and compared, comprising the steps of: folding each fabric in the same way such that each fabric has 2 folds; placing the folded fabric on a background surface to provide it with a standardized draped shape, wherein the predetermined standardized drape of the fabric comprises: a bottom ply that is on the background surface and has a first side edge; an intermediate ply having a second side edge, a first fold line between the bottom and intermediate plies; and a top ply having a third side edge; and a second fold line between the intermediate and top plies; wherein the first, second and third side edges are on the same side of the fabric; the first and third side edges are spaced apart and extend generally parallel in a first direction; the second side edge is located between the first and third side edges; and the first and second fold lines are spaced apart and extend generally parallel in a second direction; and then photographing each draped and folded fabric in a first same way.

5. The method of claims 4, 1, 2 or 3 wherein the second direction is substantially perpendicular to the first direction.

6. The method of claim 5 wherein the first fold line includes a first curve formed by the first and second side edges and having a first radius and wherein the second fold line includes a second curve formed by the second and third side edges and having a second radius, and wherein the first radius is smaller than the second radius.

7. The method of claim 6 wherein a portion of each draped and folded fabric, within a rectangular virtual photo frame, is photographed with a camera and wherein the first direction is at an obtuse angle with respect to a side of the virtual photo frame closest to the camera.

8. The method of claim 7 wherein the obtuse angle is between about 105° and 120°, preferably about 110°.

9. The method of claim 8 wherein the second direction is at an acute angle with respect to a side of the virtual photo frame closest to the camera and wherein the acute angle is between about 15° and 30°, preferably about 20°.

10. The method of claim 9 wherein the first, second and third side edges are serrated.

11. The method of claim 10 wherein each fabric is also photographed in a second same way as straight with a full-repeat of a pattern.

12. The method of claim 11 wherein the fabric has a serrated edge and is atop a gray background.

13. The method of claim 12 wherein each fabric is also shown in a computer-generated photo-realistic image in a third same way, in use.

14. The method of claim 13 wherein each fabric is shown in use as a window covering and/or a furniture covering.

15. The method of claim 14 wherein each photograph of a fabric in the first and/or second way is stored in a computer database and is tagged to indicate a use of the fabric.

16. The method of claim 15 wherein a plurality of pre-processed digitized photographs of 3-dimensional models of unprinted fabrics in the use are also in the database.

17. The method of claim 16 wherein the computer-generated photo-realistic image is made on demand of a purchaser by rendering the photograph of the fabric in the first or second way on the photograph of the 3-dimensional model in the use.

18. The method of claim 7 wherein the second direction is at an acute angle with respect to a side of the virtual photo frame closest to the camera and wherein the acute angle is between about 15° and 30°, preferably about 20°.

19. The method of claim 18 wherein the first, second and third side edges are serrated.

20. The method of claim 19 wherein each fabric is also photographed in second same way as straight with a full-repeat of a pattern.

21. The method of claim 20 wherein the fabric has a serrated edge and is atop a gray background.

22. The method of claim 21 wherein each fabric is also shown in a computer-generated photo-realistic image in a third same way, in use.

23. The method of claim 22 wherein each fabric is shown in use as a window covering and/or a furniture covering.

24. The method of claim 23 wherein each photograph of a fabric in the first and/or second way is stored in a computer database and is tagged to indicate a use of the fabric.

25. The method of claim 24 wherein a plurality of pre-processed digitized photographs of 3-dimensional models of unprinted fabrics in the use are also in the database.

26. The method of claim 25 wherein the computer-generated photo-realistic image is made on demand of a purchaser by rendering the photograph of the fabric in the first or second way on the photograph of the 3-dimensional model the use.

27. The method of claims 4, 1, 2, or 3 wherein the first, second and third side edges are serrated.

28. The method of claim 27 wherein each fabric is also photographed in second same way as straight with a full-repeat of a pattern.

29. The method of claim 28 wherein the fabric has a serrated edge and is atop a gray background.

30. The method of claim 29 wherein each fabric is also shown in a computer-generated photo-realistic image in a third same way, in use.

31. The method of claim 30 wherein each fabric is shown in use as a window covering and/or a furniture covering.

32. The method of claim 31 wherein each photograph of a fabric in the first and/or second way is stored in a computer database and is tagged to indicate a use of the fabric.

33. The method of claim 32 wherein a plurality of pre-processed digitized photographs of 3-dimensional models of unprinted fabrics in the use are also in the database.

34. The method of claim 33 wherein the computer-generated photo-realistic image is made on demand of a purchaser by rendering the photograph of the fabric in the first or second way on the photograph of the 3-dimensional model in the use.

35. A standardized method of reproducibly making photographs of different fabrics, so that one or more of each fabric's characteristics of texture, pattern, thickness, drape and translucency, can be reliably understood and compared, comprising the steps of: folding each fabric in the same way such that each fabric has 2 folds; placing the folded fabric on a background surface to provide it with a standardized draped shape; and then photographing a portion of each draped and folded fabric, within a rectangular virtual photo frame, in a first same way by a camera, so that the resulting photograph has a first total surface area, a second surface area of the photograph shows the fabric and a third surface area of the photograph shows the background surface; the second surface area being greater than the third surface area, and wherein a first direction is at an obtuse angle between about 105° an 120°, preferably about 110°, with respect to a side of the virtual photo frame closest to the camera and a second direction is at an acute angle between about 15° and 30°, preferably about 20°, with respect to a side of the virtual photo frame closest to the camera; and wherein the first, second and third side edges are serrated.

36. The method of claim 35 wherein each fabric is also photographed in second same way as straight with a full-repeat of a pattern.

37. The method of claim 36 wherein the fabric has a serrated edge and is atop a gray background.

38. The method of claim 37 wherein each fabric is also shown in a computer-generated photo-realistic image in a third same way, in use.

39. The method of claim 33 wherein each fabric is shown in use as a window covering and/or a furniture covering.

40. The method of claim 39 wherein each photograph of a fabric in the first and/or second way is stored in a computer database and is tagged to indicate a use of the fabric.

41. The method of claim 40 wherein a plurality of pre-processed digitized photographs of 3-dimensional models of unprinted fabrics in the use are also in the database.

42. The method of claim 41 wherein the computer-generated photo-realistic image is made on demand of a purchaser by rendering the photograph of the fabric in the first or second way on the photograph of the 3-dimensional model in the use.

43. A standardized method of reproducibly making photographs of different fabrics, so that one or more of each fabric's characteristics of texture, pattern, thickness, drape and translucency, can be reliably understood and compared, comprising the steps of: folding each fabric in the same way such that each fabric has 2 folds; placing the folded fabric on a background surface to provide it with a standardized draped shape; and then photographing a portion of each draped and folded fabric, within a rectangular virtual photo frame, in a first same way by a camera, so that the resulting photograph has a first total surface area, a second surface area of the photograph shows the fabric and a third surface are of the photograph shows the background surface; the second surface area being greater than the third surface area, and wherein a first direction is at an obtuse angle with respect to a side of the virtual photo frame closest to the camera and a second direction is at an acute angle between about 15° and 30°, preferably about 20°, with respect to a side of the virtual photo frame closest to the camera; and wherein the first, second and third side edges are serrated.

44. The method of claim 43 wherein each fabric is also photographed in second same way as straight with a full-repeat of a pattern.

45. The method of claim 44 wherein the fabric as a serrated edge and is atop a gray background.

46. The method of claim 45 wherein each fabric is also shown in a computer-generated photo-realistic image in a third same way, in use.

47. The method of claim 46 wherein each fabric is shown in use as a window covering and/or a furniture covering.

48. The method of claim 48 wherein each photograph of a fabric in the first and/or second way is stored in a computer database and is tagged to indicate a use of the fabric.

49. The method of claim 48 wherein a plurality of pre-processed digitized photographs of 3-dimensional models of unprinted fabrics in the use are also in the database.

50. The method of claim 49 wherein the computer-generated photo-realistic image is made on demand of a purchaser by rendering the photograph of the fabric in the first or second way on the photograph of the 3-dimensional model the use.

51. A standardized method of reproducibly making photographs of different fabrics, so that one or more of each fabric's characteristics of texture, pattern, thickness, drape and translucency, can be reliably understood and compared, comprising the steps of: folding each fabric in the same way; placing the folded fabric on a background surface to provide it with a standardized draped shape; photographing each draped an folded fabric in a first same way; and showing each fabric in a second way in a computer-generated photo-realistic image in use as a window covering and/or a furniture covering, wherein each photograph of a fabric in the first or second way is stored in a computer database and is tagged to indicate a use of the fabric.

52. The method of claim 51 wherein a plurality of pre-processed digitized photographs of 3-dimensional models of unprinted fabrics in the use are also in the database.

53. The method of claim 52 wherein the computer-generated photo-realistic image is made on demand of a purchaser by rendering the photograph of the fabric in the first or second way on the photograph of the 3-dimensional model in the use.

54. A standardized method of reproducibly making photographs of different fabrics, so that one or more of each fabric's characteristics of texture, pattern, thickness, drape and translucency, can be reliably understood and compared, comprising the steps of: folding each fabric in the same way; placing the folded fabric on a background surface to provide it with a standardized draped shape; photographing each draped and folded fabric in a first same way; and showing each fabric in a second way in a computer-generated photo-realistic image, in use, wherein each photograph of a fabric in the first and/or second way is stored in a computer database and is tagged to indicate a use of the fabric.

55. The method of claim 54 wherein a plurality of pre-processed digitized photographs of 3-dimensional models of unprinted fabrics in the use are also in the database.

56. The method of claim 55 wherein the computer-generated photo-realistic image is made on demand of a purchaser by rendering the photograph of the fabric in the first or second way on the photograph of the 3-dimensional model in the use.

57. A standardized method of reproducibly making photographs of different fabrics, so that one or more of each fabric's characteristics of texture, pattern, thickness, drape and translucency, can be reliably understood and compared, comprising the steps of: folding each fabric in the same way; placing the folded fabric on a background surface to provide it with a standardized draped shape; photographing each draped and folded fabric in a first same way; and photographing each fabric in a second same way as straight with a full-repeat of a pattern.

58. The method of claim 57 wherein the fabric has a serrated edge and is atop a gray background.

59. The method of claim 58 wherein each fabric is also shown in a computer-generated photo-realistic image in a third same way, in use.

60. The method of claim 59 wherein each fabric is shown in use as a window covering and/or a furniture covering.

61. The method of claim 60 wherein each photograph of a fabric in the first and/or second way is stored in a computer database and is tagged to indicate a use of the fabric.

62. The method of claim 61 wherein a plurality of pre-processed digitized photographs of 3-dimensional models of imprinted fabrics in the use are also in the database.

63. The method of claim 62 wherein the computer-generated photo-realistic image is made on demand of a purchaser by rendering the photograph of the fabric in the first or second way on the photograph of the 3-dimensional model in the use.

* * * * *

UNITED STATES PATENT AND TRADEMARK OFFICE
CERTIFICATE OF CORRECTION

PATENT NO. : 6,832,125 B2
DATED : December 14, 2004
INVENTOR(S) : David Sonnenberg et al.

It is certified that error appears in the above-identified patent and that said Letters Patent is hereby corrected as shown below:

Column 13,
Line 57, delete "are" and insert -- area --; and

Column 14,
Line 26, delete "an" and insert -- and --.

Signed and Sealed this

Twelfth Day of April, 2005

JON W. DUDAS
*Director of the United States Patent and Trademark Office*